United States Patent [19]

Martani et al.

[11] Patent Number: 4,780,322

[45] Date of Patent: Oct. 25, 1988

[54] METHOD OF PRODUCING SLOW-RELEASE PHARMACEUTICAL FORMS

[75] Inventors: Rosa Martani; Elisabeth Le Huede; Jeanne Dumas, all of Bordeaux, France

[73] Assignee: Societe Cortial, S.A., Paris, France

[21] Appl. No.: 820,151

[22] Filed: Jan. 21, 1986

[30] Foreign Application Priority Data

Jan. 21, 1985 [FR] France ................................ 85 00878

[51] Int. Cl.$^4$ ........................... A61K 9/22; A61K 9/52
[52] U.S. Cl. ..................................... 424/501; 424/81; 424/497; 514/944; 514/964; 514/965
[58] Field of Search ........................ 514/944, 964, 965; 424/81, 33, 32, 20, 19, 497, 501

[56] References Cited

U.S. PATENT DOCUMENTS

| 3,108,044 | 10/1963 | Rety et al. | 521/32 |
|---|---|---|---|
| 3,138,525 | 6/1964 | Koff | 521/33 |
| 3,594,470 | 7/1971 | Borodkin et al. | 424/16 |
| 3,608,063 | 9/1971 | Banker | 424/33 |
| 4,013,820 | 3/1977 | Farhadieh et al. | 514/964 |
| 4,499,066 | 2/1985 | Moro et al. | 424/81 |
| 4,514,385 | 4/1985 | Damani et al. | 424/81 |
| 4,606,909 | 8/1986 | Bechgaard et al. | 424/35 |
| 4,618,491 | 10/1986 | Kanematu et al. | 424/81 |
| 4,693,887 | 9/1987 | Shah | 424/81 |

FOREIGN PATENT DOCUMENTS 2147002  5/1985  United Kingdom ............... 514/964

Primary Examiner—Ronald W. Griffin
Attorney, Agent, or Firm—Oblon, Fisher, Spivak, McClelland & Maier

[57] ABSTRACT

The invention relates to a novel method of producing slow-release pharmaceutical forms administered per os, by simultaneously employing two resins having anionic character, the proportions of said resins being variable.

By varying the ratio of the amounts of active principles on the respective two resins, it is possible to modify the release kinetics of active principle; and by independently varying the amount of carboxylic resin it is possible to produce stabile pharmaceutical preparations which are in liquid, semi-liquid, or solid form.

22 Claims, 5 Drawing Sheets

METHOD OF PRODUCING SLOW-RELEASE PHARMACEUTICAL FORMS

BACKGROUND OF THE INVENTION

1. Field of the Invention

The invention relates to methods of producing slow-release pharmaceutical forms.

2. Discussion of the Background

A variety of alternative methods for producing slow-release pharmaceutical forms have already been described in a number of patents. For example:

The active principles may be diluted in an inert pulverulent excipient mixture, to which a surfactant is added (French Patent Nos. 82-13 613 and 82-04 672);

The principle of a matrix of a film may be employed. This matrix may or may not be embedded in an outer material or coated (Belgian Patent No. 783,661; French Patent Nos. 82-18 407, 82-21 109, 79-28 056, 76-30 362, and 72-19 993);

The active principles may be embedded in spherules or particles of a phospholipid (French Patent No. 76-02 016);

Complexes based on an ion exchange resin are employed, without being embedded or coated (Belgian Patent No. 876,857; European Patent No. 80 870 032.2; British Patent Nos. 1,576,016, 982,150, and 824,337; and French Patent No. 72-30 623);

The complex between the resin and the medicament may be treated with a solvating agent, and is provided with a water-permeable coating which forms a diffusion barrier (French Patent No. 77-35 611; U.S. Pat. No. 3,138,525; and British Patent No. 1,218,102).

All these inventions are principally concerned with galenic solid forms. Slow-release forms which involve liquid homogeneous forms are rare.

SUMMARY OF THE INVENTION

Accordingly, it is an object of this invention to provide a method for preparing a galenic preparation.

It is another object of this invention to provide a method for preparing a galenic preparation which can be administered per os.

It is another object of this invention to provide a method for preparing a galenic preparation, administered per os, which provides slow release of the active principle.

It is another object of this invention to provide a method for producing such preparations which are especially stable.

It is another object of this invention to provide a method for producing such preparations wherein their dissolution kinetics can be adjusted at will.

The inventors have now surprisingly discovered that a method for preparing such formulations, which makes use of two anionic resins employed simultaneously, in variable proportions, satisfies all of the above objects of this invention. The resins used have the property of fixing the active principles to form complexes between the respective resin and the active principles. The resins used are a sulfonate resin and a carboxylic resin.

The present invention also provides the slow-release formulation produced by this method.

BRIEF DESCRIPTION OF THE DRAWINGS

A more complete appreciation of the invention and many of the attendant advantages thereof will readily obtained as the same becomes better understood by reference to the following detailed description when considered in connection with the accompanying figures, wherein FIGS. I-IV illustrate variation of the slow-release kinetics as a function of the ratio of the amounts of active principle fixed to each of the two resins, for various active principles. The active principles are metoclopramide, codeine, dextromethorphan and ethylmorphine for FIGS. I, II, III and IV, respectively.

FIG. V shows the dissolution kinetics for metoclopramide as a function of pH.

DETAILED DESCRIPTION OF THE PREFERRED EMBODIMENTS

Figure 1:
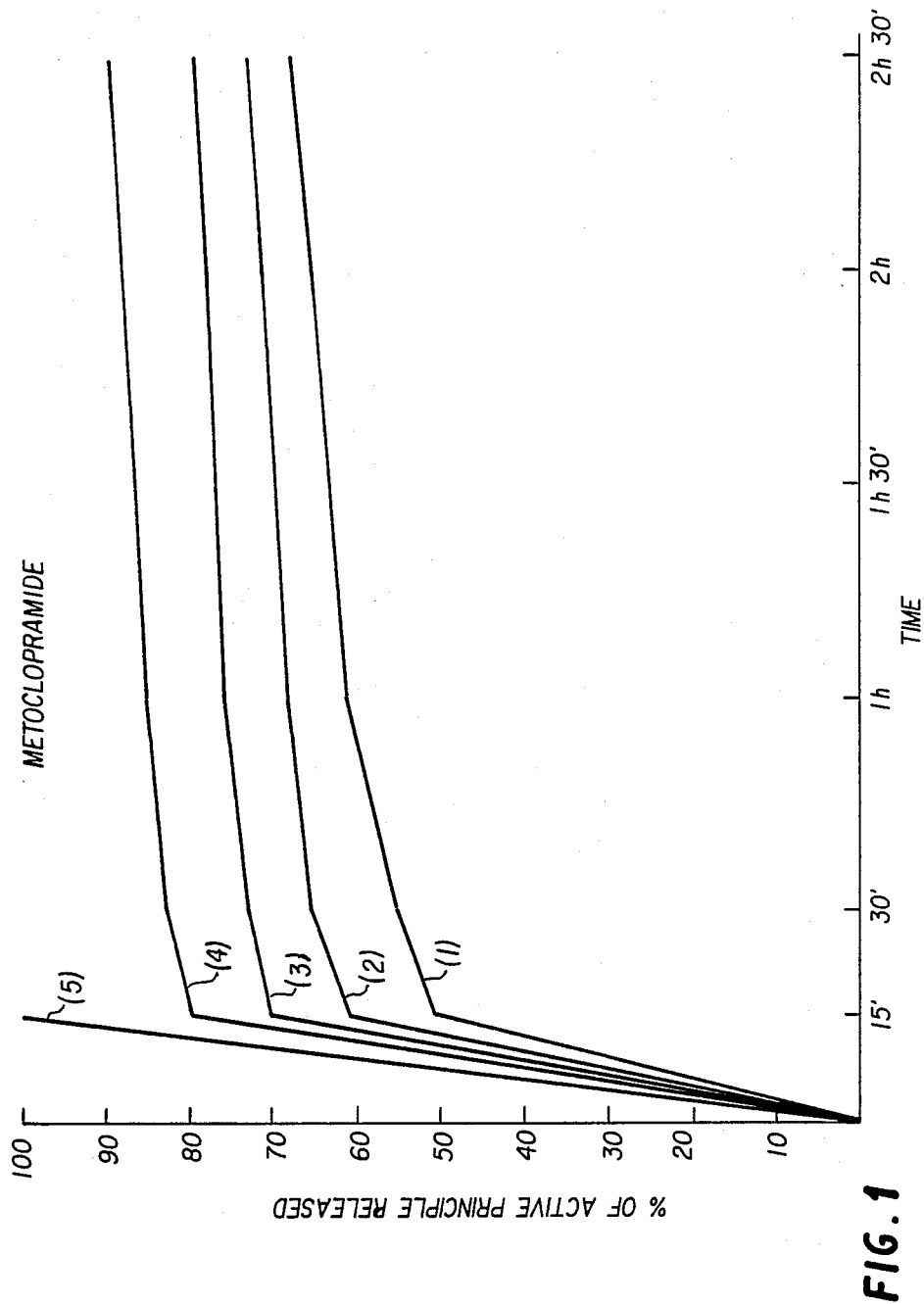
Figure 2:
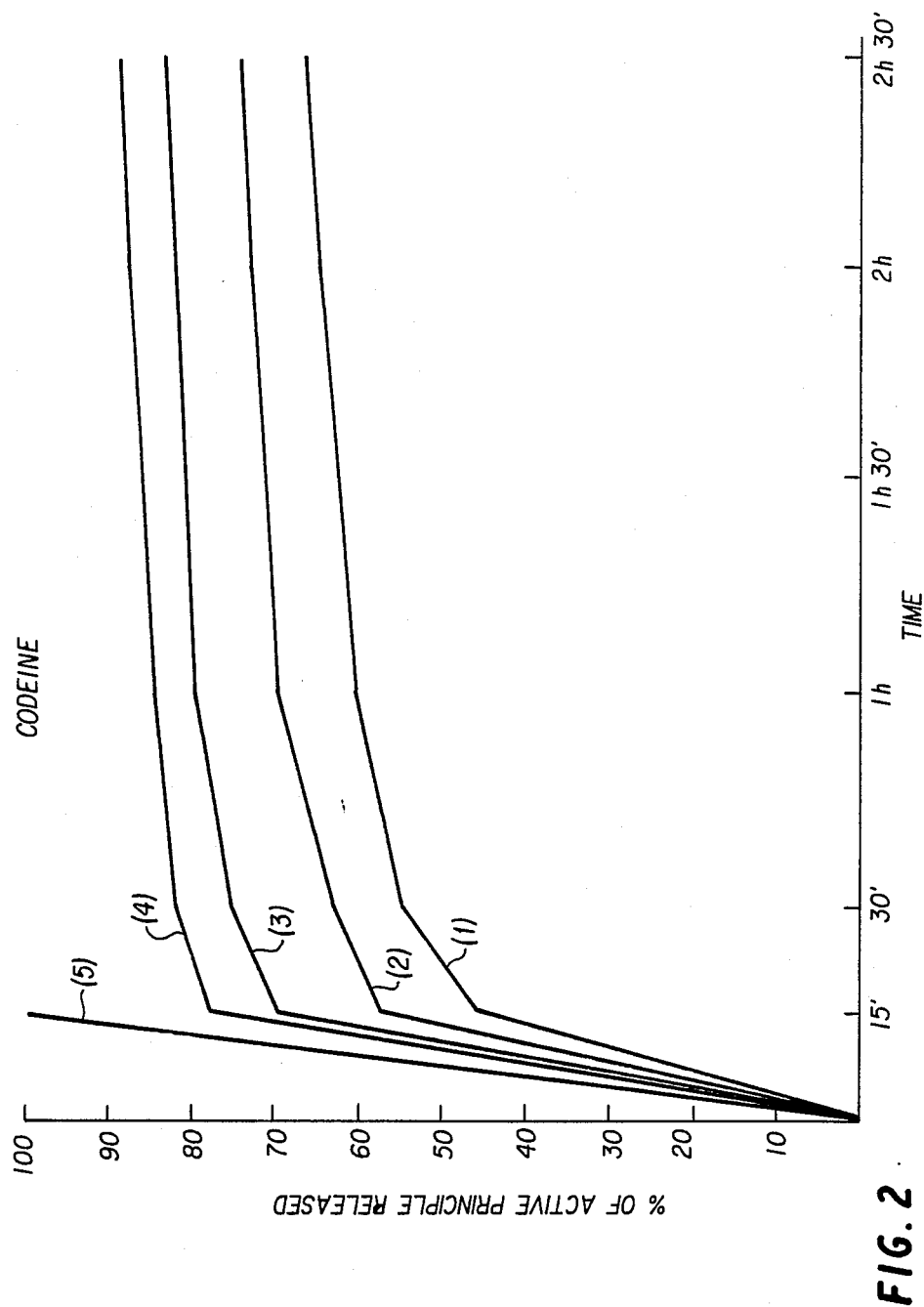
Figure 3:
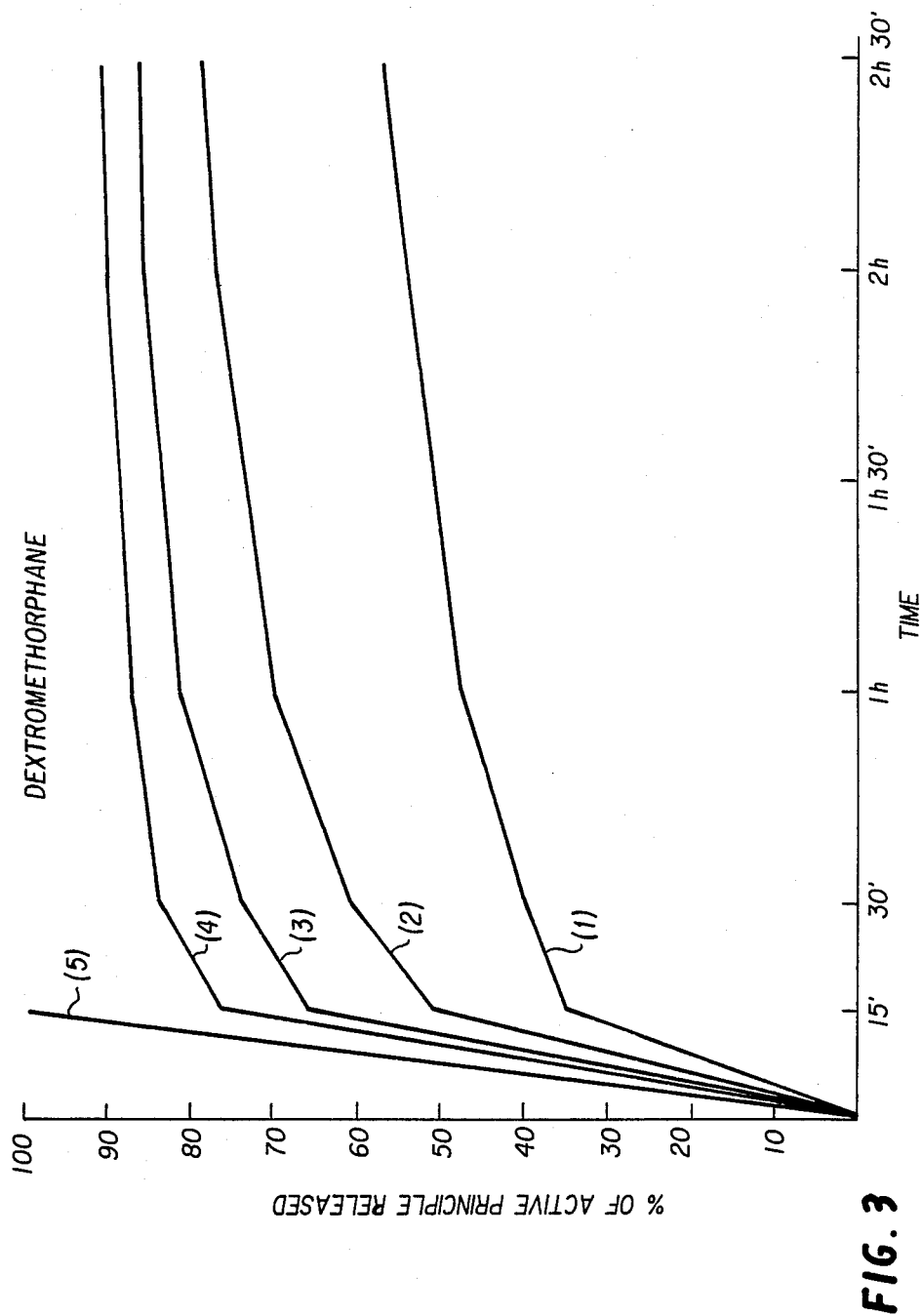
Figure 4:
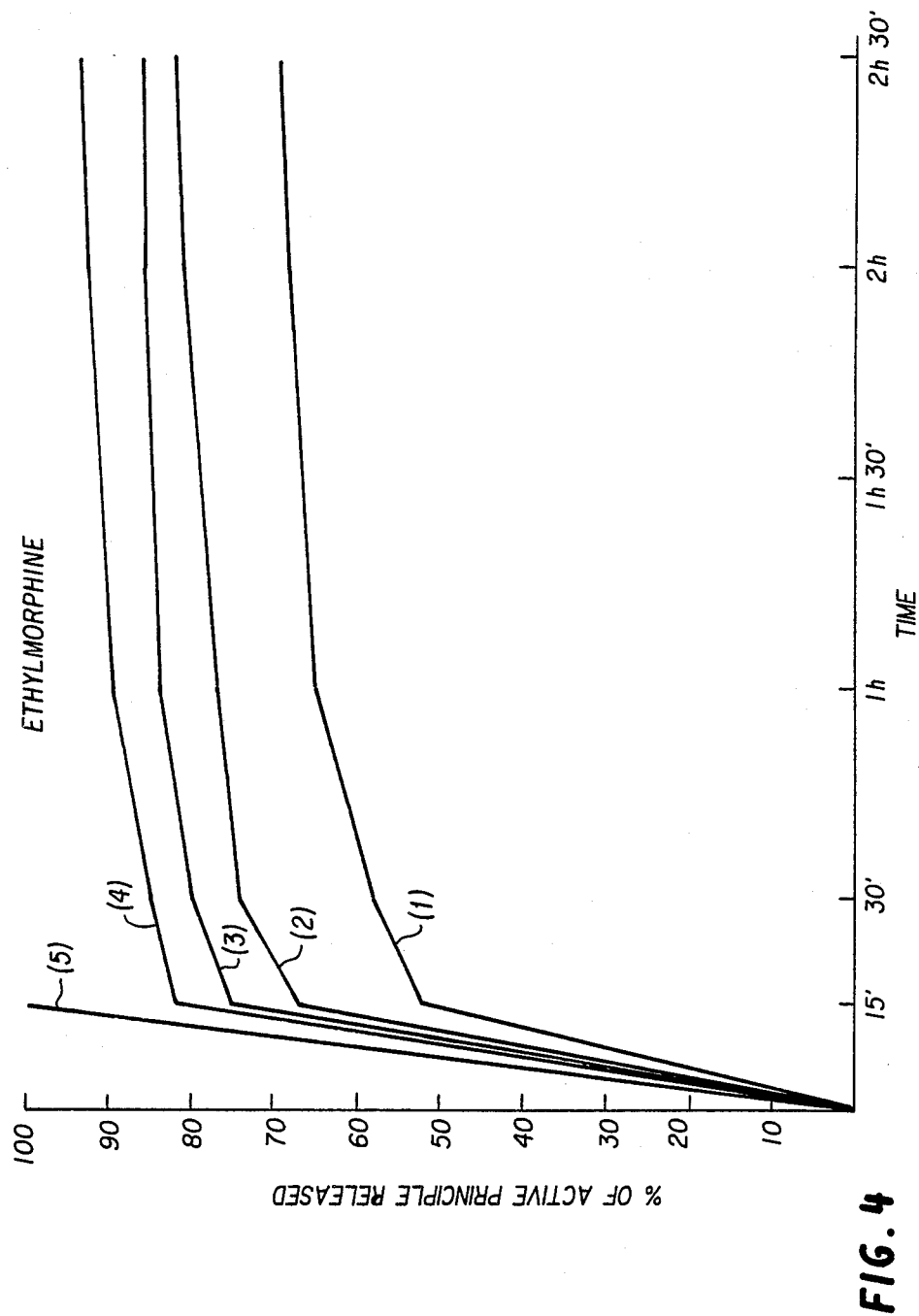
Figure 5:
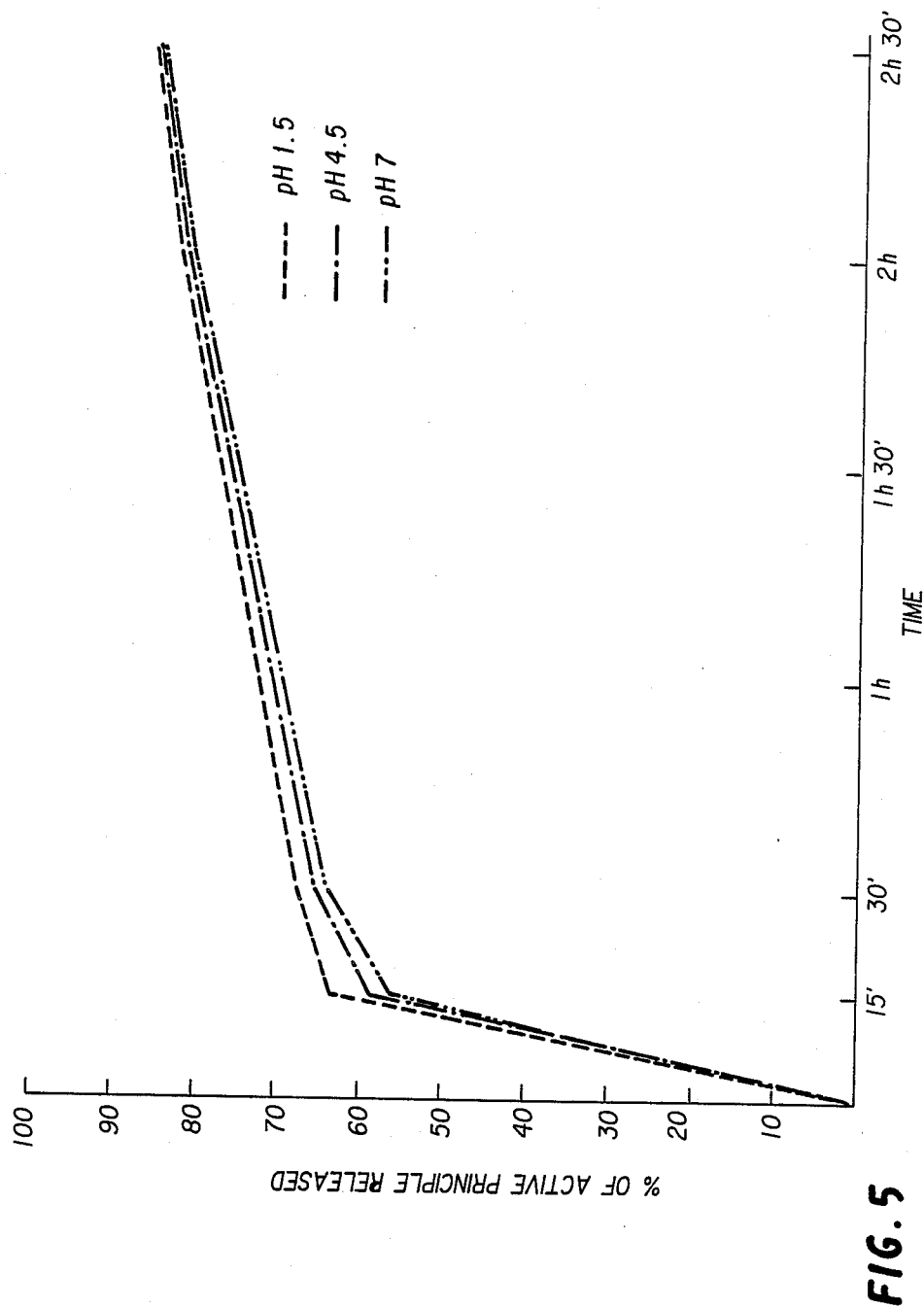

The sulfonate resin releases the active principle slowly. This resin comprises a crosslinked polymer containing sulfonate groups, with the crosslinking agent being divinylbenzene.

The degree of crosslinking is in the neighborhood of 7 to 9%, preferably 8%, and the particle sizes are <200 microns. The amount of active principle fixed to the resin may vary from 30 to 70 wt. %.

The carboxylic resin releases the active principle much more rapidly. This resin may be a carboxymethylcellulose-based resin (a monofunctional cationic ion exchange medium), but a "carbomer" (a crosslinked polymer of acrylic acid, of high molecular weight and containing carboxylate groups in the amount of 56–68 wt. %) is preferably used.

In this connection and with regard to the carboxylic resin, although various patents, particularly U.S. Pat. No. 3,594,470, mention the use of this carboxylic resin, its use is only disclosed for the purpose of masking the taste of active principles. The carboxylic resin disclosed in U.S. Pat. No. 3,594,470 is a cationic exchange resin containing free carboxylic acid groups to which a basic reacting drug can be absorbed, column 2, lines 3–7. There is no patent which proposed to employ this resin as developed in the present invention, where the resin has two functions:

(1) Fixing the active principle; and (2) Serving as a suspending or gelifying agent in the case of the liquid or gel form of the pharmaceutical, or as a matrix in the case of the solid form of the pharmaceutical.

It has been found by the present inventors that:

By varying the ratio of the amounts of the active principles fixed on the two resins (i.e., the ratio of the amount of active principle on the first resin to that on the second), it is possible to adjust the release kinetics of the active principles; and By varying the amount of the carboxylic resin it is possible to obtain—by virtue of their hydrocolloid character—pharmaceutical preparations which are in the form of liquids, semi-liquids, gels of greater or lesser thickness, compressed tablets, or powders for administration in gel capsules, packets, etc.

The preparations thus obtained are completely stable, and their dissolution kinetics are not sensitive to pH.

The method is of interest for all active principles having a cationic character and a short half-life. This invention applies particularly to: Metoclopramide hydrochloride, dextromethorphan hydrobromide, and salts of morphine and of morphine derivatives.

Other features of the invention will become apparent in the course of the following descriptions of exemplary embodiments which are given for illustration of the invention and are not intended to be limiting thereof.

A. Adjustment of the release kinetics

By varying the amounts of active principle fixed on each of the two resins, we have obtained different dissolution kinetics as measured by the official method known as the "rotating vane method" (Propharmacopeia Note No. 79):

| | Example for metoclopramide | | | | |
|---|---|---|---|---|---|
| TIME | A 100%–B 0% (1) | A 75%–B 25% (2) | A 50%–B 50% (3) | A 25%–B 75% (4) | A 0%–B 100% (5) |
| 15 minutes | 51% | 61% | 70% | 80% | 100% |
| 30 minutes | 55% | 65% | 73% | 83% | — |
| 1 hour | 61% | 68% | 76% | 85% | — |
| 2 hours | 65% | 71% | 78% | 88% | — |

Key to the Table: (A) Proportion of the active principle fixed to the sulfonate resin; (B) Proportion of the active principle fixed to the carboxylic resin.

The results from this table are illustrated in FIG. I which clearly shows the variation of the kinetics as a function of the ratio of the amounts of active principle fixed to each of the two resins.

The more the amount of active principle fixed to the carboxylic resin becomes dominant, the more the amount of active principle released in the first minutes is increased.

FIGS. II, III, and IV illustrate the results for other active principles (codeine, dextromethorphan, and ethylmorphine, respectively) impregnated on or into the same resins.

It turns out that:

(a) In the first five minutes, the amount of active principle released is a function of the amount of active principle fixed to the carboxylic resin. In the subsequent minutes, the release curves have slopes which are close to each other in value.

(b) The use of the said two resins simultaneously thus permits the dose of active principle which one desires to have been released after the first minutes to be chosen, this choice being accomplished by varying the ratio of the amounts fixed to each of the two respective resins.

(c) Also, the dissolution kinetics are not influenced by the pH (see FIG. V, which illustrates the case for metoclopramide).

B. Production of different galenic forms

Because of the hydrocolloid character of the carboxylic resin, the carboxylic resin enables the following to be produced:

Liquids—for percentages of the carboxylic resin, with respect to the total weight of both resins, present on the order of 0.05 to 0.5 Wt. %, Semi-liquids—for percentages on the order of 0.50 to 1.0 wt. %;

Gels—for percentages on the order of 1 to 2 wt. %. and

Solids (powders, compressed tablets, gel capsules, et.)—for percentages on the order of 1 to 10 wt. %.

The methods of producing these galenic forms do not present any particular difficulties; no matter the active principle used, the manufacturing technique is basically the same:

For liquid and gel forms:

Stage 1: Impregnation of the sulfonate resin with the specified quantity of the active principle; and Stage 2: Solubilization of the carboxylic resin ("carbomer") fixation of the remaining active principle which is to be added, and incorporation of excipients and of the impregnated sulfonate resin. The amount of carbomer employed is a function of the viscosity desired (e.g., whether the final product is to be a suspension, a gel, etc.).

For solid forms:

By dry mixing of the resins impregnated with the exipients, one obtains compressed tablets or powders having kinetic parameters which correspond to the relative amounts of active principle impregnated on or into the two respective resins.

Obviously, numerous modifications and variations of the present invention are possible in light of the above teachings. It is therefore to be understood that within the scope of the appended claims, the invention may be practiced otherwise than as specifically described herein.

What is claimed as new and desired to be secured by Letters of the United States is:

1. A method for producing a slow-release pharmaceutical preparation, said method consisting essentially of combining two resins having anionic character with an active cationic principle, wherein the first resin is a sulfonate resin and the second resin is a carboxylic resin comprising a cationic exchange resin which has free carboxylic acid groups to which a basic reacting drug can be absorbed.

2. The method of claim 1, said method comprising varying the relative amounts of the said active principle fixed on the two said resins to adjust the release kinetics of the slow-release pharamceutical preparation.

3. The method of claim 1, said method comprising independently varying the amount of the said carboxylic resin in the said preparation to produce a stable slow-release pharmaceutical preparation in liquid, semi-liquid, gel, powder or compressed tablet form, wherein the release kinetics of the said active principle are not influenced by variations in pH.

4. A method for producing a slow-release pharmaceutical preparation consisting essentially of combining one or more cationic drugs with two anionic resins, wherein the said first resin is a polystyrene resin containing sulfonate groups, and the second resin is a carboxyvinyl polymer resin or a carboxymethyl cellulose resin.

5. A slow-release pharmaceutical preparation, consisting essentially of a sulfonate resin and a carboxylic resin in combination with an active principle, wherein the said active principle has a cationic character and a short-half-life.

6. The slow-release pharamceutical preparation of claim 5, wherein the said active principle is at least one member selected from the group consisting of metoclopramide, codeine, dextromethorphan, morphine, morphine derivatives exclusive of their salts and salts thereof.

7. The slow-release pharmaceutical preparation of claim 6, wherein the said active principle comprises metoclopramide or a salt thereof.

8. The slow-release pharamceutical preparation of claim 6, wherein the said active principle comprises codeine or a salt thereof.

9. The slow-release pharmaceutical preparation of claim 6, wherein the said active principle comprises dextromethorphan or a salt thereof.

10. The slow-release pharmaceutical preparation of claim 6, wherein the said active principle comprises morphine or a morphine derivative.

11. The slow-release preparation of claim 5, wherein the said sulfonate resin comprises a crosslinked polymer containing sulfonate groups.

12. The slow-release preparation of claim 11, wherein the crosslinking agent of the said crosslinked polymer is divinylbenzene.

13. The slow-release prepartion of claim 11, wherein the degree of crosslinking is in the neighborhood of 7–9%, and the said crosslinked polymer is in the form of particles of less than 200 microns in size.

14. The slow-release preparation of claim 11, wherein form 30 to 70 wt. % of the said active principle is fixed to the said sulfonate resin.

15. The slow-release preparation of claim 5, wherein the said carboxylic resin is a carboxymethyl cellulose resin.

16. The slow-release preparation of claim 5, wherein the said carboxylic resin is a high molecular weight crosslinked polymer of acrylic acid, containing 56 to 68 wt. % carboxylate groups.

17. The slow-release pharamceutical preparation of claim 5, wherein the said preparation is in the form of a liquid, a semi-liquid, a gel, a compressed tablet, a powder or a packet.

18. The slow-release pharmaceutical preparation of claim 5, wherein the rate of delivery of the said active principle is not influenced by variations in pH.

19. A slow-release pharmaceutical preparation consisting essentially of one or more cationic drugs with two anionic resins, wherein the first resin is a polystyrene resin containing sulfonate groups, and the second resin is a carboxyvinyl polymer resin or a carboxymethyl cellulose resin.

20. A method for administering a pharmaceutically active principle, consisting essentially of:
 (i) combining the said pharamceutically active principle with a sulfonate resin and a carboxylic resin, and
 (ii) administering the combination of step (i).

21. The method of claim 20, comprising adjusting the kinetics of administration of the said pharmaceutically active principle by varying the relative amounts of active principle fixed on the two resins respectively.

22. The method of claim 20, comprising fixing from 30 to 70 wt. % of the said active principle to the said sulfonate resin, prior to adminstration.

* * * * *